US005616475A

United States Patent [19]
Wachsman et al.

[11] Patent Number: 5,616,475
[45] Date of Patent: Apr. 1, 1997

[54] HUMAN T-CELL LEUKEMIA VIRUS TRANSCRIPTION MODULATORS AND SCREENING ASSAYS

[75] Inventors: William Wachsman, Encinitas; Tracy Martin, Coronado; Wolfgang Klump, Del Mar, all of Calif.

[73] Assignee: The Regents of the University of California, Oakland, Calif.

[21] Appl. No.: 383,761

[22] Filed: Feb. 3, 1995

[51] Int. Cl.$^6$ .............................. C12P 21/06; C12N 1/00; C12N 5/10; C12N 15/12
[52] U.S. Cl. ..................... 435/69.1; 435/243; 536/23.5
[58] Field of Search ..................... 536/23.5; 435/240.2, 435/240.1, 69.1, 243

[56] References Cited

PUBLICATIONS

Jones et al., "Marek Disease Virus Encodes a Basic–leucine Zipper Gene Resembling the *fos/jun* Oncogenes that is Highly Expressed in Lymphoblastoid Tumors", *Proc. Natl. Acad. Sci. USA* 89:4042–4046 (1992).

Nyborg et al., "Binding of Host–cell Factors to DNA Sequences in the Long Terminal Repeat of Human T–cell Leukemia Virus Type I: Implications for Viral Gene Expression", *Proc. Natl. Acad. Sci. USA* 85:1457–1461 (1988).

Schütte et al., "*jun–B* inhibits and c–fos Stimulates the Transforming and Trans–Activating Activities of *c–jun*", *Cell* 59:987–997 (1989).

*Primary Examiner*—Mindy Fleischer
*Assistant Examiner*—Terry A. McKelvey
*Attorney, Agent, or Firm*—Richard Aron Osman

[57] ABSTRACT

The invention provides methods and compositions relating to the Tax-response Complex-1 (TRC-1) a transcription complex associated with disease, particularly HTLV infection. TRC-1 is composed of novel forms of JunB and a member of a novel protein family called small nuclear factors or SNFs. The expression of these compounds are shown to correlate with cell lineage, activation and infection. SNFs and T-cell specific forms of JunB, find particular use in screening assays for agents or lead compounds for agents useful in the diagnosis, prognosis or treatment of disease, particularly HTLV infection. Nucleic acids encoding SNFs, and SNF-specific binding agents find use in diagnosis and as commercial reagents for the biopharmaceutical industry.

17 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 223 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

```
GGGGCAGACG TGGGACGGGA AGGACGGCTG CCGGGACTGG CGCGCGGGGA CACTGGGCCG        60
ACGCGTGGAG TAGCGGGGAG AGCGGGAAGC CTGAGGGGGC GGGGCCGGCG CGAGGCCGTG       120
GGTGCGGCAC GAGGATGCCG GCGGCGGGAC AGCGCCCGTA GGCAGCCCCA CGGGCAGGGC       180
GCGCGGGCGG GGCGGGGCGG GCCGGGCCAG AGGAGCGCCC GGC                        223
```

( 2 ) INFORMATION FOR SEQ ID NO:2:

( i ) SEQUENCE CHARACTERISTICS:
( A ) LENGTH: 90 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..90

( x i ) SEQUENCE DESCRIPTION: SEQ ID NO:2:

```
ATG  TCG  CAA  GGG  CTC  CCG  GCC  GCC  GGC  AGC  GTC  CTG  CAG  AGG  AGC  GTC    48
Met  Ser  Gln  Gly  Leu  Pro  Ala  Ala  Gly  Ser  Val  Leu  Gln  Arg  Ser  Val
  1                5                    10                   15

GCG  GCG  CCC  GGG  AAC  CAG  CCG  CAG  CCG  CAG  CCG  CAG  CAG  CAG                90
Ala  Ala  Pro  Gly  Asn  Gln  Pro  Gln  Pro  Gln  Pro  Gln  Gln  Gln
             20                   25                   30
```

( 2 ) INFORMATION FOR SEQ ID NO:3:

( i ) SEQUENCE CHARACTERISTICS:

( A ) LENGTH: 30 amino acids
            ( B ) TYPE: amino acid
            ( D ) TOPOLOGY: linear ( i i ) MOLECULE TYPE: protein ( x i ) SEQUENCE DESCRIPTION: SEQ ID NO:3:

Met Ser Gln Gly Leu Pro Ala Ala Gly Ser Val Leu Gln Arg Ser Val
 1               5                  10                  15

Ala Ala Pro Gly Asn Gln Pro Gln Pro Gln Pro Gln Gln Gln
             20                  25                  30

( 2 ) INFORMATION FOR SEQ ID NO:4:

( i ) SEQUENCE CHARACTERISTICS:
            ( A ) LENGTH: 105 base pairs
            ( B ) TYPE: nucleic acid
            ( C ) STRANDEDNESS: double
            ( D ) TOPOLOGY: linear ( i i ) MOLECULE TYPE: cDNA ( i x ) FEATURE:
            ( A ) NAME/KEY: CDS
            ( B ) LOCATION: 1..105

( x i ) SEQUENCE DESCRIPTION: SEQ ID NO:4:

AGC CCT GAG GAT GAT GAC AGG AAG GTC CGA AGG AGA GAA AAA AAC CGA    48
Ser Pro Glu Asp Asp Asp Arg Lys Val Arg Arg Arg Glu Lys Asn Arg
             35                  40                  45

GTT GCT GCT CAG AGA AGT CGG AAG AAG CAG ACC CAG AAG GCT GAC AAG    96
Val Ala Ala Gln Arg Ser Arg Lys Lys Gln Thr Gln Lys Ala Asp Lys
             50                  55                  60

CTC CAT GAG                                                       105
Leu His Glu
         65

( 2 ) INFORMATION FOR SEQ ID NO:5:

( i ) SEQUENCE CHARACTERISTICS:
            ( A ) LENGTH: 35 amino acids
            ( B ) TYPE: amino acid
            ( D ) TOPOLOGY: linear ( i i ) MOLECULE TYPE: protein ( x i ) SEQUENCE DESCRIPTION: SEQ ID NO:5:

Ser Pro Glu Asp Asp Asp Arg Lys Val Arg Arg Arg Glu Lys Asn Arg
 1               5                  10                  15

Val Ala Ala Gln Arg Ser Arg Lys Lys Gln Thr Gln Lys Ala Asp Lys
             20                  25                  30

Leu His Glu
         35

( 2 ) INFORMATION FOR SEQ ID NO:6:

( i ) SEQUENCE CHARACTERISTICS:
            ( A ) LENGTH: 156 base pairs
            ( B ) TYPE: nucleic acid
            ( C ) STRANDEDNESS: double
            ( D ) TOPOLOGY: linear ( i i ) MOLECULE TYPE: cDNA ( i x ) FEATURE:
            ( A ) NAME/KEY: CDS
            ( B ) LOCATION: 1..156

( x i ) SEQUENCE DESCRIPTION: SEQ ID NO:6:

```
AGC  CCT  GAG  GAT  GAT  GAC  AGG  AAG  GTC  CGA  AGG  AGA  GAA  AAA  AAC  CGA        48
Ser  Pro  Glu  Asp  Asp  Asp  Arg  Lys  Val  Arg  Arg  Arg  Glu  Lys  Asn  Arg
               40                        45                        50

GTT  GCT  GCT  CAG  AGA  AGT  CGG  AAG  AAG  CAG  ACC  CAG  AAG  GCT  GAC  AAG        96
Val  Ala  Ala  Gln  Arg  Ser  Arg  Lys  Lys  Gln  Thr  Gln  Lys  Ala  Asp  Lys
               55                        60                        65

CTC  CAT  GAG  AAC  TTA  TTA  ATG  ACT  TGG  ATG  AAG  AAA  AGG  AAG  ACC  TGT       144
Leu  His  Glu  Asn  Leu  Leu  Met  Thr  Trp  Met  Lys  Lys  Arg  Lys  Thr  Cys
               70                        75                        80

GTG  TTA  AGT  TAG                                                                   156
Val  Leu  Ser  *
               85
```

( 2 ) INFORMATION FOR SEQ ID NO:7:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Ser  Pro  Glu  Asp  Asp  Asp  Arg  Lys  Val  Arg  Arg  Arg  Glu  Lys  Asn  Arg
 1                   5                        10                       15

Val  Ala  Ala  Gln  Arg  Ser  Arg  Lys  Lys  Gln  Thr  Gln  Lys  Ala  Asp  Lys
               20                        25                       30

Leu  His  Glu  Asn  Leu  Leu  Met  Thr  Trp  Met  Lys  Lys  Arg  Lys  Thr  Cys
               35                        40                       45

Val  Leu  Ser
          50
```

( 2 ) INFORMATION FOR SEQ ID NO:8:

( i ) SEQUENCE CHARACTERISTICS:
        ( A ) LENGTH: 129 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..129

( x i ) SEQUENCE DESCRIPTION: SEQ ID NO:8:

```
GCT  CAG  AGA  GAA  TCC  TCA  GCG  GCT  TGG  GCC  CAG  CAC  AGG  AGA  GGT  CAC        48
Ala  Gln  Arg  Glu  Ser  Ser  Ala  Ala  Trp  Ala  Gln  His  Arg  Arg  Gly  His
          55                        60                        65

TGC  CAC  ACA  TTT  GCC  CTT  GGC  ATG  GTC  TCC  AGA  ACC  ATG  CAT  TGC  ATC        96
Cys  His  Thr  Phe  Ala  Leu  Gly  Met  Val  Ser  Arg  Thr  Met  His  Cys  Ile
          70                        75                        80

CTG  GGA  GCA  ACA  TTT  TCT  GAG  ATA  TTC  TGG  TAA                               129
Leu  Gly  Ala  Thr  Phe  Ser  Glu  Ile  Phe  Trp  *
 85                        90                        95
```

( 2 ) INFORMATION FOR SEQ ID NO:9:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Ala | Gln | Arg | Glu | Ser | Ser | Ala | Ala | Trp | Ala | Gln | His | Arg | Arg | Gly | His |
|---|---|---|---|---|---|---|---|---|---|---|---|---|---|---|---|
| 1 | | | | 5 | | | | | 10 | | | | | 15 | |

| Cys | His | Thr | Phe | Ala | Leu | Gly | Met | Val | Ser | Arg | Thr | Met | His | Cys | Ile |
|---|---|---|---|---|---|---|---|---|---|---|---|---|---|---|---|
| | | | 20 | | | | 25 | | | | | 30 | | | |

| Leu | Gly | Ala | Thr | Phe | Ser | Glu | Ile | Phe | Trp |
|---|---|---|---|---|---|---|---|---|---|
| | | 35 | | | | 40 | | | |

( 2 ) INFORMATION FOR SEQ ID NO:10:

( i ) SEQUENCE CHARACTERISTICS:
        ( A ) LENGTH: 189 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..189

( x i ) SEQUENCE DESCRIPTION: SEQ ID NO:10:

| GAA | TAT | GAG | AGC | CTG | GAG | CAA | CAA | AAC | ACC | ATG | CTG | CGG | AGA | GAG | ATC | 48 |
|---|---|---|---|---|---|---|---|---|---|---|---|---|---|---|---|---|
| Glu | Tyr | Glu | Ser | Leu | Glu | Gln | Gln | Asn | Thr | Met | Leu | Arg | Arg | Glu | Ile | |
| 45 | | | | | 50 | | | | | 55 | | | | | | |

| GGG | AAG | CTG | ACA | GAG | GAG | CTG | AAG | CAC | CTG | ACA | GAG | GCA | CTG | AAG | GAG | 96 |
|---|---|---|---|---|---|---|---|---|---|---|---|---|---|---|---|---|
| Gly | Lys | Leu | Thr | Glu | Glu | Leu | Lys | His | Leu | Thr | Glu | Ala | Leu | Lys | Glu | |
| 60 | | | | | 65 | | | | | 70 | | | | | 75 | |

| CAC | GAG | AAG | ATG | TGC | CCG | CTG | CTG | CTC | TGC | CCT | ATG | AAC | TTT | GTG | CCA | 144 |
|---|---|---|---|---|---|---|---|---|---|---|---|---|---|---|---|---|
| His | Glu | Lys | Met | Cys | Pro | Leu | Leu | Leu | Cys | Pro | Met | Asn | Phe | Val | Pro | |
| | | | | 80 | | | | | 85 | | | | | 90 | | |

| GTG | CCT | CCC | CGG | CCG | GAC | CCT | GTG | GCC | GGC | TGC | TTG | CCC | CGA | TGA | | 189 |
|---|---|---|---|---|---|---|---|---|---|---|---|---|---|---|---|---|
| Val | Pro | Pro | Arg | Pro | Asp | Pro | Val | Ala | Gly | Cys | Leu | Pro | Arg | * | | |
| | | | 95 | | | | 100 | | | | | 105 | | | | |

( 2 ) INFORMATION FOR SEQ ID NO:11:

( i ) SEQUENCE CHARACTERISTICS:
        ( A ) LENGTH: 62 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| Glu | Tyr | Glu | Ser | Leu | Glu | Gln | Gln | Asn | Thr | Met | Leu | Arg | Arg | Glu | Ile |
|---|---|---|---|---|---|---|---|---|---|---|---|---|---|---|---|
| 1 | | | | 5 | | | | | 10 | | | | | 15 | |

| Gly | Lys | Leu | Thr | Glu | Glu | Leu | Lys | His | Leu | Thr | Glu | Ala | Leu | Lys | Glu |
|---|---|---|---|---|---|---|---|---|---|---|---|---|---|---|---|
| | | | 20 | | | | 25 | | | | | 30 | | | |

| His | Glu | Lys | Met | Cys | Pro | Leu | Leu | Leu | Cys | Pro | Met | Asn | Phe | Val | Pro |
|---|---|---|---|---|---|---|---|---|---|---|---|---|---|---|---|
| | | 35 | | | | 40 | | | | | 45 | | | | |

| Val | Pro | Pro | Arg | Pro | Asp | Pro | Val | Ala | Gly | Cys | Leu | Pro | Arg |
|---|---|---|---|---|---|---|---|---|---|---|---|---|---|
| | 50 | | | | 55 | | | | | 60 | | | |

( 2 ) INFORMATION FOR SEQ ID NO:12:

( i ) SEQUENCE CHARACTERISTICS:
        ( A ) LENGTH: 390 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:12:

| | | | | | | |
|---|---|---|---|---|---|---|
| AGCCGGGGAC | ACTCCTCTGC | CCAGCAAGGA | GCCTTGGTCA | TTTTCATACC | TGGGAGGAAG | 60 |
| GCTTTTCCTT | CACAATTGTA | TACAGGGGGC | ACCTGTGGCC | AGGCCTCCTC | CTGGGAGCTC | 120 |
| CAGGACCAGC | CAGCTGTGTT | CCCTGCAGAC | TGGGCTCAGC | CCGACATCCA | ACAGGCGCCA | 180 |
| AACTCACAGA | GCCCTTGTGC | AGATCCAGCA | TGGAGGCCAC | CCTCAGGAGT | GACTTCTCAT | 240 |
| CCACCCTGGC | AGCTAGTAGG | TTCTGCTGTT | ATGCAGAGCC | ATTTCCTCTA | GAATTTGGAT | 300 |
| AATAAAGATG | CTTATTGTCT | CTCCCTTCTC | CAGTTCTGGG | AATTTACAGG | CACAATACAC | 360 |
| TTCCTTTTCC | TGGAAAAAAA | AAAAAAAAA | | | | 390 |

HUMAN T-CELL LEUKEMIA VIRUS TRANSCRIPTION MODULATORS AND SCREENING ASSAYS

This work was supported by grants from the Department of Veterans affairs and the National Institutes of Health. The government may have rights in any invention disclosed herein.

INTRODUCTION

1. Technical Field

The technical field of this invention concerns human T-cell leukemia virus (HTLV) transcription factors.

2. Background

The human T-cell leukemia virus types 1 (HTLV-1) and 2 (HTLV-2) are etiologic for specific T-lymphoid malignancies in humans. In addition, these retroviruses transform normal human T-cells in vitro. Although HTLV does not harbor an oncogene, it does express accessory genes, including tax, which is required in-trans for efficient viral replication. Several investigations have implicated the tax encoded protein as playing a central role in the process of oncogenesis and T-cell transformation. Tax is a nuclear phosphoprotein that, in addition to the HTLV provirus, mediates expression of many genes involved in T-cell growth and proliferation. Studies have indicated that Tax acts through several types of cis-acting sequences, including the cyclic-AMP response element (CRE), kB sites, and CArG boxes. In that Tax does not bind specifically to DNA, it is thought to act indirectly, via host cell factors, which interact with cognate DNA elements to regulate gene expression.

To gain insight as to the mechanism of Tax action and determine how this HTLV accessory factor induces lymphoid malignancy, we and others have sought cellular factors that interact with Tax-responsive DNA sequences. Several such factors have been identified by DNA binding assays. Some of these have even been cloned by probing cDNA expression libraries with Tax-responsive sequences. These various host cell factors have, however, invariably been shown to exist in both non-HTLV- and HTLV-transformed cells.

RELEVANT LITERATURE

Jones et al. (1992) PNAS 89:4042–4046 discloses a viral gene with some sequence similarity to the disclosed snf gene.

Nyborg, J K, W S Dynan, I S Chen, W Wachsman (1988), Proc Natl Acad Sci U S A 85:1457–1461 describes HTLV LTR binding proteins in HTLV-transformed T cells.

Schuette, J, M et al. (1989), Cell 59: 987–997, describes the cloning of human junB cDNA and functional analysis of JunB in epithelial cells.

Other potentially relevant papers include: Jeang, K T, et al. (1988), J Virol 62:4499–4509; Nyborg, J K, et al. (1990)J Biol Chem 265:8230–8236; Yoshimura T, et al. (1990)Embo J 9:2537–2542; Zhao, L J, et al. (1991) Proc Natl Acad Sci U S A 88:11445–11449; Tsujimoto, A, et al. (1991) J Virol 65:1420–1426.

JunB phosphorylation papers include: Grover-Bardwick A, et al. (1994) Carcinogenesis 15:1667–1674; Coffer P, et al. (1994) Oncogene 9: 911–921; Nikolakaki E, et al. (1993) Oncogene 8:833–840; Schonthal A, et al. (1991) New Biologist 3:977–986; Franklin, C C, et al. (1992) Proc Natl Acad Sci USA 89: 7247–7251.

SUMMARY OF THE INVENTION

The invention provides methods and compositions relating to the Tax-response Complex-1 (TRC-1) a transcription complex associated with disease. TRC-1 is composed of novel forms of JunB and a member of a novel protein family called small nuclear factors or SNFs.

In one embodiment, the invention provides isolated SNFs, comprising the translation product of at least one of SNF exon 1 (SEQ ID NO:3), exon 2 (SEQ ID NO:5), exon 2b (SEQ ID NO:7), exon 3 (SEQ ID NO:9), exon 4 (SEQ ID NO: 11), or a fragment thereof having an SNF-specific binding affinity. Functionally, exon 1 encodes a glutamine-proline rich domain critical for cellular activation and transformation; exon 2 encodes a basic domain important for proper nucleic acid binding; and exon 4 encodes a leucine zipper. SNF-binding affinities may be shown by competitively inhibiting SNF-mediated transcription, SNF—Jun binding, etc. The invention provides nucleic acid encoding SNFs, which nucleic acids may be part of SNF-expression vectors and may be incorporated into a recombinant cell. The invention provides agents which selectively bind SNF's or bind to disrupt the binding of SNF to intracellular targets and methods of making such agents.

SNFs find particular use in screening assays for agents or lead compounds for agents useful in the diagnosis, prognosis or treatment of disease, particularly HTLV infection. One such assay involves forming both a first mixture comprising an SNF, an intracellular SNF binding target, and a prospective agent at a first concentration and a second mixture comprising the same SNF, the same intracellular SNF binding target and the same prospective agent at a second concentration different from the first concentration. Typically, the second mixture is a negative control (i.e. the agent concentration is zero). The mixtures are incubated to permit the binding of the intracellular SNF binding target to the SNF and the mixtures are then analyzed for the presence of such binding. A difference in such binding between the first and second mixtures indicates that the agent is capable of disrupting the binding of SNF to an intracellular SNF binding target and the agent is an agent or a lead compound for an agent useful in the diagnosis, prognosis or treatment of disease.

In another embodiment, the invention provides novel forms of JunB having novel phosphorylation patterns, methods and reagents for detecting these novel JunB forms, and methods of use. For example, the regional expression of these novel forms of JunB is show to correlate with cell lineage, activation and infection.

DETAILED DESCRIPTION OF THE INVENTION

The invention provides methods and compositions relating to TRC-1 and its substituent components, particularly new forms of JunB and SNFs—a novel family of transcription factors. SNFs are characterized by having a translation product of at least one of SNF exon 1 (SEQ ID NO:3), exon 2 (SEQ ID NO:5), exon 2b (SEQ ID NO:7), exon 3 (SEQ ID NO:9), exon 4 (SEQ ID NO: 11). A wide variety of exon combinations and alternatively spliced forms of SNF may be used. Exon splicing combinations found in HTLV transformed T-cells include 1–3 (72 amino acids which encompass the activation domain but lack both the basic DNA binding and leucine zipper domains); 1–2b (81 amino acids wherein the splice site at the end of exon 2 is ignored and a downstream alternative splice is used—this variant lacks a leucine zipper domain); 1–2–3 (107 amino acids which encompass the activation and basic DNA binding domains but due to a stop codon in exon three contains no leucine zipper domain); and 1–2–4 (127 amino acids which encompass the activation, the basic DNA binding and leucine zipper domains). The translation products of all five exons and nucleic acids comprising wild-type coding sequences for these exons are shown in SEQ ID NOS:3, 5, 7, 9 and 11 and SEQ ID NOS: 2, 4, 6, 8 and 10 respectively. The 5' and 3' untranslated regions which comprise gene expression regulating sequences of the wild-type SNFs are shown in SEQ ID NOS: 1 and 12, respectively.

The subject SNFs and SNF fragments have one or more SNF-specific binding affinities, i.e. the ability to specifically bind at least one natural intracellular SNF binding target or a SNF-specific binding agent such as a SNF-specific antibody or a SNF-specific binding agent identified in assays as described below. Exemplary natural intracellular binding targets include nucleic acids which comprise one or more SNF DNA binding sites such as the 21 bp HTLV LTR sequence described below, transcription factors such as JunB, structurally related factors (e.g. other bZIP proteins). Other natural SNF binding targets are readily identified by screening cells, membranes and cellular extracts and fractions with the disclosed materials and methods and by other methods known in the art. For example, two-hybrid screening using alternative SNF exon products or portions thereof are used to identify intracellular targets which bind specific SNF portions. Preferred SNF fragments retain the ability to complex with T-cell derived JunB to form TRC-1. Convenient ways to verify the ability of a given SNF fragment to form such a complex include in vitro labelled binding assays such as described below, and EMSAs.

A wide variety of molecular and biochemical methods are available for generating and expressing SNF fragments, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. For example, SNF or fragments thereof may be obtained by chemical synthesis, expression in bacteria such as *E. coli* and eukaryotes such as yeast or vaccinia or baculovirus-based expression systems, etc., depending on the size, nature and quantity of the SNF or fragment. The subject SNF fragments are of length sufficient to provide a novel peptide. As used herein, such peptides are at least 5, usually at least about 6, more usually at least about 8, most usually at least about 10 amino acids. SNF fragments may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc. The subject SNF fragments maintain binding affinity of not less than six, preferably not less than four, more preferably not less than two orders of magnitude less than the binding equilibrium constant of a full-length native SNF to the binding target under similar conditions. Some SNF fragments or deletion routants, in particular SNFs with C-terminus truncations, are shown to function in a dominant-negative fashion. Similarly, chimeric proteins including a fusion to the amino terminus of the translation product of SNF exon 1, or fragments thereof comprising that fusion junction, are shown to prevent phosphorylation of the SNF activation domain. Such fragments provide therapeutic agents, particularly when delivered by intracellular immunization—transfection of susceptible cells with nucleic acids encoding such mutants.

The claimed SNFs and SNF fragments are isolated, partially pure or pure and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample.

The invention provides SNF-specific binding agents, methods of identifying and making such agents, and their use in diagnosis. For example, SNF-specific agents are useful in a variety of diagnostic applications, especially where disease or disease prognosis is associated with the expression of SNF or TRC-1, e.g. HTLV infection. Novel SNF-specific binding agents include JunB with phosphorylation patterns resulting from expression in T-cells, particularly activated T-cells and especially HTLV-infected T-cells; SNF-specific antibodies; novel nucleic acids with sequence similarity to that of the 21 bp repeat of the HTLV LTR as described below; other natural intracellular binding agents identified with assays such as one- and two-hybrid screens; non-natural intracellular binding agents identified in screens of chemical libraries, etc.

Generally, SNF-specificity of the binding target is shown by binding equilibrium constants. Such targets are capable of selectively binding a SNF, i.e. with an equilibrium constant at least about $10^4 M^{-1}$, preferably at least about $10^6 M^{-1}$, more preferably at least about $10^8 M^{-1}$. A wide variety of cell-based and cell-free assays may be used to demonstrate SNF-specific binding. Cell based assays include one and two-hybrid screens, mediating or competitively inhibiting SNF-mediated transcription, etc. Preferred are rapid in vitro, cell-tree assays such as mediating or inhibiting SNF-protein (e.g. SNF-JunB binding), SNF-nucleic acid binding, immunoassays, etc. Other useful screening assays for SNF/SNF fragment-target binding include fluorescence resonance energy transfer (FRET), electrophoretic mobility shift analysis (EMSA), etc.

The invention also provides nucleic acid encoding SNFs, which nucleic acids may be part of SNF-expression vectors and may be incorporated into recombinant cells for expression and screening, transgenic animals for functional studies (e.g. the efficacy of candidate drugs for disease associated with expression of a SNF), etc. In addition, the invention provides nucleic acids sharing substantial sequence similarity with that of one or more wild-type SNF nucleic acids (SEQ ID NOS: 1, 2, 4, 6, 8, 10, 12). Substantially identical or homologous nucleic acid sequences hybridize to their respective complements under high stringency conditions, for example, at 55° C. and hybridization buffer comprising 50% formamide in 0.9M saline/0.09M sodium citrate (SSC) buffer and remain bound when subject to washing at 55° C. with the SSC/formamide buffer. Where the sequences diverge, the differences are preferably silent, i.e. or a nucleotide change providing a redundant codon, or conservative, i.e. a nucleotide change providing a conservative amino acid substitution. Such nucleic acids find particular use as hybridization probes, PCR primers, therapeutic nucleic acids, etc.

for use in detecting the presence of SNF genes and gene transcripts, for detecting or amplifying nucleic acids with substantial sequence similarity such as SNF homologs and structural analogs, and for gene therapy applications. Given the subject probes, materials and methods for probing CDNA and genetic libraries and recovering homologs are known in the art. Preferred libraries are derived from human immune cells, especially CDNA libraries from differentiated and activated or infected human lymphoid cells. SNF encoding nucleic acids also find applications in gene therapy. For example, nucleic acids encoding dominant-negative SNF mutants are cloned into a virus and the virus used to transfect and confer HTLV resistance to T-cells.

Therapeutic SNF nucleic acids are used to modulate, usually reduce, cellular expression or intracellular concentration or availability of active SNFs. These nucleic acids are typically antisense: single-stranded sequences comprising complements of the disclosed SNF nucleic acids. Antisense modulation of SNF expression may employ SNF antisense nucleic acids operably linked to gene regulatory sequences. Cell are transfected with a vector comprising a SNF sequence with a promoter sequence oriented such that transcription of the gene yields an antisense transcript capable of binding to endogenous SNF encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a SNF or SNF fragment may be administered to the target cell at a concentration that results in a substantial reduction in SNF expression.

The subject nucleic acids are often recombinant, meaning they comprise a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The invention provides efficient methods of identifying pharmacological agents or drugs which are active at the level of SNF modulatable cellular function, particularly TRC-1 formation and gene transcription. Generally, these screening methods involve assaying for compounds which interfere with SNF activity such as SNF-Jun B binding, TRC-1 complex formation, TRC-1-DNA binding, etc. The methods are amenable to automated, cost-effective high throughput drug screening and have immediate application in a broad range of domestic and international pharmaceutical and biotechnology drug development programs.

Target therapeutic indications are limited only in that the target cellular function (e.g. gene expression) be subject to modulation, usually inhibition, by disruption of the formation of a complex (e.g. transcription complex) comprising one or more of the SNFs and one or more natural SNF intracellular binding targets. Since a wide variety of genes are subject to SNF regulated gene transcription, target indications may include viral, bacterial and fungal infections, metabolic disease, genetic disease, cell growth and regulatory disfunction, such as neoplasia, inflammation, hypersensitivity, etc. Frequently, the target indication is an undesirable infection, particularly an HTLV infection.

A wide variety of assays for binding agents are provided including labelled in vitro protein-protein and protein-DNA binding assay, electrophoretic mobility shift assays, immunoassays for protein binding or TRC-1 complex formation, cell base assays such as one, two and three hybrid screens, expression assays such as transcription assays, etc. For example, three-hybrid screens are used to rapidly examine the effect of transfected nucleic acids, which may, for example, encode combinatorial peptide libraries or antisense molecules, on the intracellular binding of SNFs to SNF targets. Convenient reagents for such assays (e.g. GAL4 fusion partners) are known in the art.

SNF or SNF fragments used in the methods are usually added in an isolated, partially pure or pure form and are typically recombinantly produced. The SNF or fragment may be part of a fusion product with another peptide or polypeptide, e.g. a polypeptide that is capable of providing or enhancing protein-protein binding, sequence-specific nucleic acid binding or stability under assay conditions (e.g. a tag for detection or anchoring).

The assay mixtures comprise at least a portion of a natural intracellular SNF binding target such as a JunB isoform or a nucleic acid comprising a sequence which shares sufficient sequence similarity with a gene or gene regulatory region to which the native SNF naturally binds to provide sequence-specific binding of the SNF or SNF fragment. Such a nucleic acid may further comprise one or more sequences which facilitate the binding of a second transcription factor or fragment thereof which cooperatively binds the nucleic acid with the SNF (i.e. at least one increases the affinity or specificity of the DNA binding of the other). While native binding targets may be used, it is frequently preferred to use portions (e.g. peptides, nucleic acid fragments) or analogs (i.e. agents which mimic the SNF binding properties of the natural binding target for the purposes of the assay) thereof so long as the portion provides binding affinity and avidity to the SNF conveniently measurable in the assay. Binding sequences for other transcription factors may be found in sources such as the Transcription Factor Database of the National Center for Biotechnology Information at the National Library for Medicine, in Faisst and Meyer (1991) Nucleic Acids Research 20, 3–26, and others known to those skilled in this art.

Where used, the nucleic acid portion bound by the peptide(s) may be continuous or segmented and is usually linear and double-stranded DNA, though circular plasmids or other nucleic acids or structure analogs may be substituted so long as SNF or TRC-1 sequence-specific binding is retained. In some applications, supercoiled DNA provides optimal sequence-specific binding and is preferred. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp. Additional nucleotides may be used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors. In addition, the nucleic acid can comprise a cassette into which transcription factor binding sites are conveniently spliced for use in the subject assays.

The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharities, fatty acids, steroids, purines, pyrimidines, derivatives, structural analogs or combinations thereof, and the like. Where the agent is or is encoded by a transferred nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the SNF specifically binds the cellular binding target, portion or analog. The mixture components can be added in any order that provides for the requisite bindings. Incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the SNF and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. For cell based assays such as one, two, and three hybrid screens, the transcript resulting from SNF-target binding usually encodes a directly or indirectly detectable product (e.g. galactosidase activity, luciferase activity, etc.). For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening. Candidate agents shown to inhibit SNF-target binding or transcription complex formation provide valuable reagents to the pharmaceutical industries for animal and human trials.

The following examples are offered by way of illustration and not by way of limitation.

EXAMPLES

Materials and Methods

Cell culture

All T-cell lines were cultured in Iscove's modified Dulbecco's media (IMDM) supplemented with 1% pen/strep and L-glutamine, as well as, with fetal bovine serum (FBS). Medium for the Jurkat and CEM T-cell lines contained 10% and 5% FBS, respectively. The HTLV-1-transformed SLB-I and ATL-1K T-cell lines and the HTLV-2-transformed Mo-T line were cultured in the same medium with 20% FBS. IMDM+10% FBS was used for culture of the gibbon ape leukemia virus-transformed MLA-144 T-cell line. HepG2 cells were cultured in Dulbecco's modified eagles media containing 1 gm/L glucose and 10% FBS. HeLa cells were cultured in Spinner flasks in Joklik's medium+10% FBS.

Oligonucleotide preparation

Oligonucleotides were synthesized using an Applied Biosystems, Inc. model 380 synthesizer with phosphoramidite chemistry. Complementary oligonucleotides were annealed, as indicated, and used in electrophoretic mobility shift assays (EMSA) or UV-crosslinking studies, as described below. In the latter, BrdU was substituted for thymidine, as part of the synthetic process, at the sites denoted in the oligonucleotide sequence.

Nuclear extract preparation and fractionation

Nuclear extracts were prepared as previously described. In brief, harvested cells were washed twice with phosphate buffered saline (PBS) containing 0.1% $MgCl_2$ and resuspended in 4× packed cell volume of hypotonic buffer (10 mM Tris/HCl pH 7.9, 10 mM KCl, 1.5 mM $MgCl_2$, and 1 mM DTT) containing a protease inhibitor cocktail of 50 mM PMSF and 1 mg/ml each of aprotinin, pepstatin A, leupeptin, and soybean trypsin inhibitor. After dounce homogenization, nuclei were washed and then extracted in hypertonic buffer (50 mM Tris/HCl pH 7.9, 420 mM KCl, 5 mM $MgCl_2$, 0.1 mM EDTA, 2 mM DTT, 20% glycerol, and 10% sucrose) containing the protease inhibitor cocktail. After sedimentation of cell debris (15,000 rm, 30 m, 4° C.), analytical scale preparations were precipitated with $(NH_4)_2SO_4$ (0.33 g/ml supernatant). The precipitate was centrifuged (15,000 ×g, 20 m, 4° C.), resuspended in TM buffer containing the protease inhibitor cocktail and then dialyzed overnight. The resultant extract was aliquoted and stored at −80° C.

For preparative scale nuclear extracts, approximately $10^{10}$ SLB-I T-cells were harvested, the nuclei isolated and lysed, as above. Precipitation with ammonium sulfate and subsequent dialysis was omitted. Instead, crude SLB-I nuclear extract was centrifuged (200,000×g, 60 m, 4° C.), diluted 4-fold with Z buffer (25 mM HEPES-KOH pH 7.8; 12.5 mM $MgCl_2$; 1 mM DTT; 20% (v/v) glycerol; 50 mM PMSF; and 0.1% Nonidet P-40), and immediately applied to heparin-agarose (5 ml HiTrap Heparin column, Pharmacia-LKB Biotechnology, Inc.). The column was washed with 10–15 ml of Z buffer containing 0.15M KCl and eluted by step gradient with 20 ml Z buffer+0.45M KCl and then with 10 ml Z buffer+0.8M KCl. TRC-1 active fractions, as determined by EMSA, were pooled, diluted with Z buffer to reduce the conductivity below that of Z buffer+0.15M KCl, and loaded onto an FPLC MonoS column (HR 5/5 MonoS, Pharmacia-LKB Biotechnology, Inc.). This column was washed with 5 ml Z buffer+0.15M KCl and eluted by linear gradient FPLC, with a total of 20 ml Z buffer, between 0.15 and 0.65M KCl, followed by step elution with 5 ml Z buffer 0.8M KCl. TRC-1 active fractions were pooled, diluted approximately 3-fold with Z buffer, adjusted with poly (dI-dC) to 1 mg/ml, and after 30 m on ice, applied to a site2 DNA-agarose affinity column that was prepared according to Kadonaga et al. The loaded DNA-affinity column was washed with Z buffer+0.06M KCl and FPLC eluted with a total of 20 ml of Z buffer by linear gradient from 0.06 to 1M KCl. Fractions were aliquoted, flash frozen in liquid nitrogen, and stored at −80° C. Aliquots were assayed for TRC-1 activity by EMSA using a site2 probe, as described above. Samples were also analyzed by SDS-PAGE on a 12% gel according to the method of Laemmli. Partial amino acid sequence analysis of TRC-1 polypeptides, fractionated through the s2 DNA-affinity stage of purification, was performed as previously described.

EMSA and UV-crosslinking assay

Crude or partially fractionated nuclear extract was preincubated for 30 m on ice in binding buffer (12.5 mM HEPES-KOH pH 7.9, 4.2 mM Tris, 83.3 mM KCl, 41.7 mM NaCl, 0.25 mM EDTA, 6.3 mM $MgCl_2$, 5 mM DTT, and 12.5% (v/v) glycerol) containing 1 mg poly(dI-dC), and 10 mg bovine serum albumin (BSA). With DNA-affinity purified protein only 0.2 mg poly(dI-dC) was used. After preincubation, radiolabelled probe with or without cold competitor oligonucleotide probe was added and incubated on ice for 30 m. After addition of 1 ml dye, samples were loaded on a 5% non-denaturing polyacrylamide gel and electrophoresed at 400 V for 2 h at 4° C. in 0.4× TBE (36 mM Tris-borate pH 8.4 and 8 mM EDTA). Subsequently gels were dried and subjected to autoradiography.

For UV-crosslinking assay one of the plates was removed from the EMSA gel. This was placed on a transilluminator (Fotodyne Foto UV 440) gel side down and irradiated at 300 nm for 30 m while being cooled with a cooling cushion of blue ice placed on top of the remaining plate. Bands indicative of DNA-protein complexes were localized by autoradiography and excised. These gel slices were boiled in 5× sample buffer (150 mM Tris/HCl pH 6.8, 25% (v/v) glycerol, 1.8 mM b-mercaptoethanol, and 5% SDS), placed into slots of a SDS-polyacrylamide gel (12%), and subjected to electrophoresis for 8 h at 100 V in Laemmli running buffer. The gel was then dried and autoradiographed.

HTLV-1 Tax protein, used in EMSA, was isolated from bacteria transformed with the pTaxH6 expression construct, as previously described. Tax protein fractions eluted from the Ni-NTA resin (Qiagen) were analyzed by SDS-PAGE on a 10% gel. Fractions containing a single protein band, as determined by silver staining the gel, were pooled and assayed for total protein content.

TRC-1 Reconstitution analysis

TRC-1 active eluate from FPLC MonoS purified SLB-I nuclear extract was subjected to SDS-PAGE (12% gel). Without staining, the gel was sliced and protein in the gel slices was eluted and renatured, as described by Briggs et al, with the following modifications. After crushing the gel slices, protein was eluted with buffer containing 0.044 mg/ml BSA, precipitated with 6× volume acetone, and dissolved in EMSA buffer without DTT, but containing 6M guanidinium hydrochloride. Renaturation was accomplished by chromatography on P6-DG resin (Biorad, Inc.). The sample was equilibrated and eluted with EMSA buffer without DTT. The alesalted protein eluate was adjusted to 10 mM DTT. DNA binding activity of the renatured protein was determined by EMSA, as described above.

Western analysis

Protein samples were subjected to SDS-PAGE with or without precipitation. In the latter, sample was precipitated with 80% trichloroacetic acid containing 4 mg/ml sodium deoxycholate, washed twice with acetone, dissolved in sample buffer, boiled for 5 m, and loaded onto the gel. Protein in the gel was electrophoretically transferred to Immobilon-P PVDF membranes (Millipore, Inc.) at 100–150 mA for 30–60 m using transfer buffer containing 39 mM glycine, 48 mM Tris, 0.037% SDS, and 20% methanol. The membranes were blocked with 5% reconstituted powdered milk, incubated with primary rabbit polyclonal antibody, and then treated with anti-rabbit IgG antibody coupled to horse radish peroxidase (Amersham, Inc.).

Antibody-protein complexes were detected by enhanced chemiluminescence (ECL)(Amersham, Inc.).

Results

HTLV is known to infect and replicate in many tissues, but it transforms only T cells in vivo. Therefore, we thought that the ubiquitous nature of these various factors, which bind to Tax-responsive cis-acting elements, mitigated their potential relevance to the process of HTLV-induced T-cell transformation. To overcome this potential limitation, we sought to identity Tax-responsive factors specifically expressed in HTLV-transformed T-cells. We disclose here the identification and characterization of Tax-response complex-1 (TRC-1), a factor that appears to be restricted in its expression to HTLV-transformed T cells. TRC-1 is a heteromultimer composed of differentially phosphorylated JunB and a novel 21 kDal. basic region, leucine zipper (bZIP) protein, termed small nuclear factor ($p21^{SNF1}$). In the presence of Tax, TRC-1 binds with higher affinity to a Tax-responsive cis-acting element in the HTLV-1 LTR. In addition, TRC-1 interacts specifically with both CREs and TPA-response elements (TREs), suggesting that it may alter the standard response modulated by these two distinct signal transduction pathways.

Tax-response complex-1 (TRC-1) is restricted to HTLV-transformed T cells

Earlier analysis of the HTLV-1 LTR for sites of specific protein-DNA interaction revealed at least 5 discreet sites of specific protein-DNA interaction. Interestingly, differences were observed in the pattern of DNase I footprinting obtained with crude nuclear extracts prepared from HTLV-transformed T cell lines versus non-HTLV-immortalized cell lines. This finding was supported by EMSA data using a HTLV-1 LTR 21-bp repeat (site2) probe, in which the specific binding of factors contained in nuclear extract from the CEM T-cell line was compared with extract from the HTLV-1-transformed SLB-I T-cell line. These observations suggested that one or more nuclear factors that bind the HTLV-1 LTR may be highly restricted to HTLV-transformed T cells.

To begin to define the basis of this DNA-binding activity we first sought to determine whether it is a consistent property in HTLV-transformed T-cells. Crude nuclear extracts were prepared from a variety of cell lines and comparatively tested by EMSA using a HTLV-1 LTR site2 (s2) probe. The results showed that multiple s2 DNA-protein complexes form with all of the extracts. Of note was the presence of a dominant complex which is formed only with nuclear extracts from the HTLV-1- or HTLV-2-transformed T-cell lines. A complex with this same mobility was not detected with extract from MLA-144, a gibbon ape leukemia virus-transformed T-cell line; Jurkat or CEM, non-HTLV-transformed T-cell lines; or the non-lymphoid HepG2 and HeLa lines.

We then performed competitive EMSA, by adding unlabelled site2 (s2) oligonucleotide probe to the assay system. As the amount of unlabelled s2 probe is increased from 12.5 to 100-fold molar excess, the TRC-1 binding activity to labelled s2 probe is abolished. In contrast, a site2 oligonucleotide probe containing a mutated core sequence did not compete for TRC-1 binding activity until 200-fold molar excess was used. These data indicate that the HTLV-1-transformed SLB-I T-cell line nuclear extract contains a factor that interacts specifically with the middle 21-bp repeat in the HTLV-1 LTR. In addition, this factor, as defined by its binding activity, is apparently present only in HTLV-transformed T cells.

Of note is the finding that the site2 binding activity is present in ATL-1K cells, a T-cell line that is transformed, but non-productively infected with HTLV-1. Extract from ATL-1K does not contain detectable Tax protein. In previous studies using ATL-1K, Tax was shown to induce expression from a recombinant that placed HTLV-1 site2 sequences upstream of a thyroidinc kinase (tk) promoter. Mutation of the site2 sequence ablated the response of this tk construct to Tax in ATL-1K cells. We postulated that this DNA-binding factor, which constitutes the dominant binding complex with the HTLV-1 LTR site2, plays a role in the response of this cis-acting element to Tax. Hence, we have termed this factor Tax-response complex-1 (TRC-1).

Differential interaction of TRC-1 with the HTLV-1 LTR 21-bp repeats

Several studies have demonstrated the importance of the 21-bp repeats in HTLV-1 with respect to Tax-mediated transactivation of the LTR. Although these three repeats are imperfect, the distal (site1) and proximal (site3) repeats are closely related to the middle (site2) 21-bp repeat used in the studies above. A core sequence 5'-TGACG-3' is bounded by a block of conserved sequences, AGGC upstream and CCCC downstream, that are separated from the core motif by non-conserved sequence. Because various studies have demonstrated that subtle changes in sequences adjacent to a core element can have substantial impact on specific DNA-protein interaction, we investigated the ability of TRC-1 to bind to each of the three 21-bp repeats. Site1 and site3 oligonucleotides were used as competitors against site2 probe for TRC-1 binding in EMSA. The percentage of competition was determined by comparing the amount of retarded site2 probe to the total amount of probe in each sample. In comparison to site2 (s2), site1 (s1) and site3 (s3) competed less efficiently for TRC-1 complex formation. A 12.5-fold molar excess of unlabelled s2 competed approximately 55% of TRC-1 binding from s2 probe. Nearly 50-fold molar excess of s3 and 100-fold molar excess of s1 was needed to achieve this same level of competition. The s1 and s3 probes, however, competed much better than the mutant site2 (s2m). These data indicate that each of the repeats can interact with TRC-1 and suggest that sequences adjacent to the core 5'-TGACG-3' element influence the binding of TRC-1.

TRC-1 complexes with CRE and TRE

The core motif in the HTLV-1 LTR 21-bp repeats 5'-TGACG-3' is identical to that for the cAMP-response element (CRE), which interacts with CREB, and the related ATF binding sites. Likewise, the TPA-response element (TRE) core is, with the exception of a single nucleotide, identical to the 21-bp core. To determine whether TRC-1 interacts with these heterologous cis-acting elements we performed EMSA using a CRE, TRE, or ATF binding site probe with SLB-I nuclear extract. With each of these probes a dominant complex and several minor complexes are formed under the same conditions for optimal binding of TRC-1 to the HTLV-1 LTR site2. In controls, 100-fold molar excess of site2 competitor prevented binding of TRC-1 to site2 probe. Likewise, addition of 100-fold molar excess CRE, ATF, or TRE competitor virtually ablates the formation of this dominant and most of the minor mobility complexes to the homologous probe. Mutation of the core motif within the CRE, ATF, and TRE competitor is unable to inhibit binding of this factor to the homologous probe. Thus, the interaction of each of these probes with several of the binding factor in SLB-I nuclear extract is specific. The use of site2 as a competitor (100-fold molar excess) is observed to markedly reduce the dominant complex formation to each of these heterologous probes, while competition with mutant site2 (s2m) is not seen to effectively compete.

We then asked whether these heterologous probes could effectively compete for TRC-1 binding to site 2. The addition of 100-fold molar excess CRE, ATF, or TRE competitor virtually eliminated the formation of TRC-1 complex with site2, while the mutant CRE, ATF, and TRE competitor did not alter the binding of TRC-1 to site2. In addition, the use of heterologous competitors was not found to affect the formation of most of the minor complexes. Overall, the data indicate that TRC-1 in the SLB-I nuclear extract forms the dominant complex seen with the CRE, ATF, and TRE probes and that TRC-1 is related to the family of basic region, leucine zipper (bZIP) transcription factors composed of CREB, ATF, and AP1.

TRC-1 is a heteromultimeric factor

To begin its physical characterization, TRC-1 was purified to near homogeneity from SLB-I nuclear extract. This was accomplished by sequential chromatographic fractionation of extract on heparin agarose, MonoS, and site2 DNA-affinity resin. At each stage of purification fractions containing TRC-1 activity, as defined by binding to site2 probe on EMSA, were pooled. The analysis of crude and fractionated extract by SDS-PAGE was performed. An equivalent amount of protein (100 mg) was loaded into lanes 1–3. Lane 4 contains less than 100 ng of purified protein. It is clear that successive chromatographic fractionation reduces the number of protein components present in the crude SLB-I nuclear extract. However, not until site2 DNA-affinity chromatography is the number of polypeptide components reduced to four major bands, located at approximately 21, 40, 41, and 43 kD on a silver stained gel. This result was surprising due to the number of polypeptide species and the small size of one of the components. It is possible that all of these dominant bands compose TRC-1, thereby making it a heteromultimer. Alternatively, some of these polypeptide species could represent residual impurities or degradation products of TRC-1 fractionation.

To determine which of these polypeptides contribute to TRC-1 binding activity, we sought to reconstitute TRC-1 DNA-binding activity from these polypeptide species. This was performed by means of site2 EMSA using renatured eluant protein from gel slices of SDS-PAGE separated SLB-I nuclear extract fractionated through heparin-agarose and mono S, as described above. Following elution, precipitation, and renaturation of protein from each gel slice, the resultant material from gel slices 3 through 8 was individually tested by EMSA for binding activity to site2. As a positive control for TRC-1 activity, we used samples of SLB-I extract fractionated through the mono S step that did not undergo SDS-PAGE separation. These control extracts were subjected to the identical precipitation and renaturation treatment as was performed for the gel eluates in order to mimic reaction conditions as closely as possible. No similar binding activity is seen for eluant from any of the individual gel slices. A weak, rapid migrating EMSA band is, however, observed with eluate from gel slice 7, which contains the 21 kD polypeptide. Gel slice 4 eluant, which contains the 40–43 kD polypeptide triplet, does not have any detectable site2 DNA binding activity. When eluates from gel slices 4 and 7 were combined, a complex was formed with site2 that migrated like control TRC-1. All other combinations of eluates tested failed to reproduce this EMSA complex with site2 probe. Again, a weak, rapid migrating complex is observed in eluate combinations that contain material from gel slice 7. These data indicate that TRC-1 activity is reconstituted when components in gel slices 4 and 7 are present, suggesting that it is a heteromultimeric factor. In that the mono S fraction of SLB-I extract contains more than the 21 and 40–43 kD polypeptides in these gel slices we cannot say with assurity that these polypeptides are the precise components of TRC-1. In addition, it is possible that a factor from either slice 4 or 7 inhibits TRC-1 activity in that respective sample, and, that the addition of a another factor from the other slice serves to increase TRC-1 activity by relieving the inhibition of TRC-1 binding.

To resolve these issues, we performed UV-crosslinking of purified TRC-1 to BrdU-substituted site 2 probe. As a control we UV-crosslinked purified recombinant CREB to this same probe. The results reveal that TRC-1 yields two detectable complexes following crosslinking to site2 probe. The largest of these is a broad band that centers at approximately 57 kD. The smaller complex migrates at approximately 32 kD. In contrast, CREB crosslinked to site2 migrates as a single, tighter band at approximately 58 kD. CREB is known to exhibit binding activity as a homodimer. Monomeric CREB migrates on SDS-PAGE between 43 and 45 kD. Although exact correction for size in this system is not possible, a rough approximation places these two components in the same size range as the 21 and 40–43 kD polypeptides seen with purified TRC-1. EMSA studies with crude SLB-I nuclear extract indicated that TRC-1 bound CRE probe. Therefore, we UV-crosslinked purified TRC-1 and CREB to a BrdU-substituted CRE probe. As expects, the results with CREB show a single band that migrates at approximately 53 D (uncorrected for probe size). In comparison, crosslinking of CRE and TRC-1 again yields two major bands, one at 29 kD and the other at 51 to 56 kD. In fact, within the larger, broad band, one can discern 3 separate, but poorly resolved bands at 51, 53, and 56 kD. Again, after correction for probe, the data show that the components of TRC-1 are similar in size to the 21, 40, 41, and 43 kD dominant polypeptides purified from SLB-I nuclear extract following site2 DNA-affinity chromatography. Similarly, purified TRC-1, following UV-crosslinking to a BrdU-substituted TRE, yielded two adducts that, after correction for probe, were consistent with the size of the 21 and 40–43 kD proteins. Overall, these data indicate that TRC-1 binds to both site2, CRE, and TRE as a heteromultimer. In addition, these results demonstrate that TRC-1 site2 DNA-binding activity is composed of the 21 and 40–43 kD polypeptides.

The 40–43 kD TRC-1 polypeptides are variably phosphorylated JunB

We next sought to determine the identity of the TRC-1 polypeptides. CRE and TRE typically interact with homo- or heterodimers composed from bZIP proteins. Many of these factors, including members of CREB and Jun protein families, are 40–45 kD in size. Based on the binding of TRC-1 to these cis-acting elements and the size of the 40–43 kD component of TRC-1, we reasoned that these may be identical or related to one or more known bZIP proteins. Therefore, we performed Western analysis of various nuclear extracts and purified TRC-1 using antibodies directed against CREB, c-Jun, JunB and JunD. The data demonstrate that CREB or a related factor of approximately 40–43 kD is abundantly present in every cell line tested, including HTLV-transformed T cells (Mo-T, ATL-1K, and SLB-I) and those not infected with HTLV (HeLa, CEM, and Jurkat). Affinity-purified TRC-1, however, failed to cross-react with the anti-CREB antibody. In addition, testing fractions liner-gradient eluted from Mono S-affinity FPLC, we found that the peak of CREB-cross reactive protein did not coincide with the peak of TRC-1 activity. These data indicate that TRC-1 is not to be composed from CREB or a highly related factor.

We further tested whether the TRC-1 polypeptides are Jun-related. A Western blot of these same samples with anti-JunB polyclonal antibody revealed that all of the HTLV-transformed T-cell extracts and purified TRC-1 cross-reacted. Upon close inspection, three different species between 40 and 43 kD are discernible in the anti-JunB Western. In contrast, extracts from HeLa, CEM, and Jurkat, which are not infected with HTLV, are negative in the Western blot developed with anti-JunB antiserum. This polyclonal anti-JunB antibody was generated towards peptide sequences (amino acids 51–68) contained in murine JunB, but not in c-Jun nor JunD. Control studies confirmed that it is specifically directed against JunB and cross-reacts with both the murine and human forms of JunB. In comparison, Westerns using anti-c-Jun antibody recognized a 41 kD species in all of the samples, including TRC-1. This experiment was performed using two different anti-c-Jun antibodies generated against two separate peptides within the molecule. Unfortunately, both of these peptides are highly conserved between the three Jun species. Control Western analyses confirmed that these two anti-c-Jun antibodies cross-react with both c-Jun and JunB. Assay using antibody specifically directed against JunD did not cross-react with TRC-1 nor any of the nuclear extracts. Thus, the Western data indicate that the 40–43 kD polypeptides are identical or related to JunB. In that TRC-1 cross-reacts with a c-Jun antibody that recognizes all species of Jun, we are unable to rule out the possibility that one or more of the TRC-1 polypeptides are c-Jun or a highly related factor.

The reactivity of the JunB antibody with all three of the 40–43 kD polypeptide species indicate that these proteins are closely related. The difference in mobility on SDS-PAGE could be due to three distinct Jun species, which have a conserved epitope, degradation of a single species of Jun, and/or post-translational modification of a Jun species. Recent evidence has shown that phosphorylation of c-Jun is important for its binding to DNA, transcriptional activity, and stability. To test whether any of the 40–43 kD proteins are phosphorylated, TRC-1, fractionated through the Mono S FPLC stage of purification, was treated with calf intestinal alkaline phosphatase (CIP). Western analysis, using anti-JunB antibody, revealed that CIP-treated TRC-1 exhibits an altered pattern of mobility on SDS-PAGE. Following exposure to CIP at 37° C. for 15 m the 40–43 kD triplet is reduced to a single band that migrates at 40 kD. In contrast, control studies in which TRC-1 is incubated in the presence of CIP with incubation at 4° C. for 15 m, or without CIP at 4° C. or 37° C., no effect on the 40–43 kD TRC-1 proteins are observed. Although it is possible that two or more polypeptide species overlap, this finding suggests that the 40–43 kD polypeptide triplet is due to three JunB species that are phosphorylated to a variable extent.

To further clarify the identity of the 40–43 kD polypeptide species, we performed partial amino acid sequence analysis on purified protein. s2 DNA-affinity purified TRC-1 from SLB-I nuclear extract was separated by SDS-PAGE on a 12% gel. It was then electrotransferred to a polyvinylidene difluoride (PVDF) membrane. The membrane-bound 40–43 kD polypeptide triplet was visualized by staining with amido black dye and then digested with trypsin in situ. Two resultant peptide fragments were subjected to Edman degradation in an automated protein sequencer: the resultant sequences are 100% homologous to the sequence of human JunB. Taken together with the Western and phosphatase dam, these results indicate that the 40–43 kD polypeptide triplet is differentially phosphorylated forms of JunB protein.

Tax facilitates TRC-1 binding to site 2 in the HTLV-1 LTR

Previous investigations indicated that purified HTLV Tax protein facilitated the binding of several host cell factors to their cognate DNA sequences, possibly by enhancing their dimerization. The experimental strategy used to characterize this property of Tax is a modification of EMSA in which the amount of binding factor is titrated so as to complex with only a small percentage of DNA probe. In the presence of Tax much more specific complex is formed. This method provided a means to test whether TRC-1, with respect to its interaction with site2, is responsive to Tax.

Using a site2 probe we performed EMSA with 1 ul of purified TRC-1 in the absence of Tax. A large amount of mobility shifted complex is formed. When the amount of TRC-1 incubated with the probe is reduced by 90%, a complex that barely detectable is formed. Tax protein, expressed in bacteria as a His6 fusion at its carboxy terminus, was purified by Ni-chelation affinity chromatography to virtual homogeneity. The addition of 150 ng of purified TaxHis6 to the reaction with site2 probe and the lower amount of TRC-1 is observed to significantly enhance the formation of the mobility shift complex. The presence of Tax was found to increase the binding of purified TRC-1 to site2 probe by 2.5- to 6.5-fold, as determined by phosphorimage analysis. Neither Tax or bovine serum albumin (BSA) was observed to form a complex with the site2 probe. These result indicates that TRC-1 is, indeed, a Tax-responsive factor.

To obtain a molecular clone of $p21^{SNF}$, we performed partial amino acid sequence analysis of $p21^{SNF}$. Following electroblotting of highly purified TRC-1 from an SDS-PAGE gel, tryptic digestion of TRC-1 on the nitrocellulose membrane, the $p21^{SNF}$ band was excised and subjected to microbore HPLC fractionation. Sequence for three SNF-1 peptides was obtained. Analysis of these sequences in comparison to current protein databases did not reveal significant homology, suggesting that $p21^{SNF}$ is unique. Based on these three SNF-1 peptides we synthesized 3 sets of degenerate upstream/downstream primers that were then used for RT PCR of SLB-I mRNA. Nested PCR generated a 91 bp partial snf cDNA, on which additional primers were based. Using these secondary primers in conjunction with the original primers, PCR of SLB-I cDNA produced a 159 bp fragment that contained additional snf sequence. This 159 bp snf cDNA was then used to screen a plasmid cDNA library made from SLB-I HTLV-transformed T-cell line mRNA. Screening approximately 140,000 plasmid colonies yielded 26 positives, 23 of which were confirmed by nucleic acid sequencing to contain all 3 of the SNF peptides. Amino-terminal chemical sequence analysis of SNF purified from SLB-I cells confirmed the identity of the full length snf cDNA clone. Further sequence analysis has revealed that SNF is a novel member of the bZIP transcription factor family. A global search of the GeneBank, EMBL, and SWIS-Prot databases found conservation of SNF to all bZIP factors (i.e. Fos, FRA, c-Jun, JunB, CREB, ATF, LRF-1, etc.), with the highest level homology (52%) to the 362 amino acid EcoQ protein expressed from the Marek Disease Virus. This type of herpesvirus is etiologically associated with T-cell leukemia in infected chickens. In light of the T-cell malignancies associated with these viruses and expression of EcoQ and SNF, albeit from quite divergent sources (e.g. SNF is a cellular factor, EcoQ a viral factor), and the ability of SNF to induce "promiscuous" binding to CRE, ATF, and TRE sites, the conservation of these two proteins demonstrates their pivotal role in T-cell leukemogenesis.

Northern analysis of mRNA from various cell lines suggests that snf-1 message is constitutively expressed at high levels in only HTLV-transformed cell lines, as opposed to non-HTLV-transformed T cells, B cells, or non-lymphoid cells. Non-HTLV-transformed T-cell lines express snf 1 at very low levels. Expression of junB message was also examined. The HTLV-transformed T-cells express both snf-1 and junB messages at high levels, which is coincident with the pattern of TRC-1 expression. These data lend further support to the limited expression of TRC-1 to HTLV-transformed T cells. Both recombinant SNF-1 and JunB have been expressed in bacteria. Recombinant SNF-1, itself, exhibits low inherent DNA binding activity. Alone, neither SNF-1 or JunB extracts reconstituted TRC-1 binding activity, but combined, SNF-1 and JunB reconstituted TRC-1. SNF-1 also interacts with c-Jun to form a complex, termed TRC-2, that binds the HTLV-1 LTR site2. The data demonstrate that SNF-1 interacts with a variety of bZIP proteins and that these complexes bind to cis-acting elements both typical and atypical for those specific bZIP proteins.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid encoding at least one polypeptide selected from the group consisting of a small nuclear factor (SNF) exon 1 translation product (SEQ ID NO:3), exon 2 translation product (SEQ ID NO:5), exon 2b translation product (SEQ ID NO:7), exon 3 translation product (SEQ ID NO:9), and exon 4 translation product (SEQ ID NO:11).

2. The isolated nucleic acid according to claim 1, wherein said nucleic acid encodes an SNF protein.

3. The isolated nucleic acid according to claim 1, wherein said nucleic acid encodes an SNF protein comprising an exon 1 translation product (SEQ ID NO:3) and exon 3 translation product (SEQ ID NO:9).

4. The isolated nucleic acid according to claim 1, wherein said nucleic acid encodes an SNF protein comprising an exon 1 translation product (SEQ ID NO:3), exon 2 translation product (SEQ ID NO:5) and exon 3 translation product (SEQ ID NO:9).

5. The isolated nucleic acid according to claim 1, wherein said nucleic acid encodes an SNF protein comprising an exon 1 translation product (SEQ ID NO:3), exon 2 translation product (SEQ ID NO:5) and oxon 2b translation product (SEQ ID NO:7).

6. The isolated nucleic acid according to claim 1, wherein said nucleic acid encodes an SNF protein comprising an exon 1 translation product (SEQ ID NO:3), exon 2 translation product (SEQ ID NO:5) and exon 4 translation product (SEQ ID NO: 11).

7. The isolated nucleic acid according to claim 1, wherein said nucleic acid encodes an SNF protein comprising an exon 1 translation product (SEQ ID NO:3), exon 2 translation product (SEQ ID NO:5), exon 3 translation product (SEQ ID NO:9) and exon 4 translation product (SEQ ID NO: 11).

8. The isolated nucleic acid according to claim 1, wherein said nucleic acid hybridizes with a nucleic acid comprising at least one nucleotide sequence selected from the group consisting of SEQ ID NOS: 1, 2, 4, 6, 8, 10 and 12 under high stringency conditions.

9. An isolated nucleic acid which comprises at least one nucleotide sequence selected from the group consisting of SEQ ID NOS: 1, 2, 4, 6, 8, 10 and 12.

10. An isolated nucleic acid comprising an open reading frame encoding at least one polypeptide selected from the group consisting of an SNF exon 1 translation product (SEQ ID NO:3), exon 2 translation product (SEQ ID NO:5), exon 2b translation product (SEQ ID NO:7), exon 3 translation product (SEQ ID NO:9), and exon 4 translation product (SEQ ID NO:11), said open reading frame joined in sequence directly to a nucleotide sequence not naturally joined to said open reading frame.

11. The nucleic acid according to claim 10, wherein said open reading frame encodes an SNF protein comprising at least one polypeptide selected from the group consisting of an SNF exon 1 translation product (SEQ ID NO:3), exon 2 translation product (SEQ ID NO:5), exon 2b translation product (SEQ ID NO:7), exon 3 translation product (SEQ ID NO:9), and exon 4 translation product (SEQ ID NO:11).

12. An isolated cell comprising the nucleic acid according to claim 10.

13. An isolated cell comprising the nucleic acid according to claim 11.

14. A method of making a recombinant SNF protein, said method comprising culturing the cell according to claim 12 and recovering the SNF protein.

15. A method of making a recombinant SNF protein, said method comprising culturing the cell according to claim 13 and recovering the SNF protein.

16. An isolated nucleic acid according to claim 9, wherein said nucleic acid comprises SEQ ID NO: 1.

17. An isolated nucleic acid according to claim 9, wherein said nucleic acid comprises SEQ ID NO: 12.

* * * * *